US00PP19000P2

(12) United States Plant Patent
Gutter

(10) Patent No.: US PP19,000 P2
(45) Date of Patent: Jul. 1, 2008

(54) *SAXIFRAGA* PLANT NAMED 'ROCKLET'

(50) Latin Name: *Saxifraga×arendsii*
Varietal Denomination: Rocklet

(76) Inventor: Martien Everett Gutter, Enkhuizen (NL)

( * ) Notice: Subject to any disclaimer, the term of this patent is extended or adjusted under 35 U.S.C. 154(b) by 0 days.

(21) Appl. No.: 11/800,646

(22) Filed: May 7, 2007

(51) Int. Cl.[8] ..... A01H 5/00
(52) U.S. Cl. ..... Plt./226
(58) Field of Search ..... Plt./226, 407

*Primary Examiner*—Annette H Para

(57) ABSTRACT

A new *Saxifraga* plant, particularly distinguished by its scarlet red flower color, early flowering and compact plant habit.

1 Drawing Sheet

Latin name of the genus and species of the plant claimed: *Saxifraga×arendsii.*
Varietal denomination: 'Rocklet'.

BACKGROUND OF THE NEW PLANT

The present invention comprises a new distinct cultivar of *Saxifraga,* botanically known as *Saxifraga×arendsii.*

The new *Saxifraga* is a product of a planned breeding program conducted in a green house in Enkhuizen, Netherlands. The new *Saxifraga* cultivar has a compact plant habit, a scarlet red flower color and an early flowering.

The new *Saxifraga* is propagated by cuttings resulting from a single seedling. This seedling originates from a red flowering selection in *Saxifraga×arendsii* 'Purperteppich' (not patented), identified as number 'D702.' This selection was made through three cycles of half sib selection. The selection was done in the period April 2001 until March 2003 in Enkhuizen, The Netherlands. The seedling was selected in March 2003 in Enkhuizen.

The present cultivar has been repeatedly asexually reproduced by cuttings in Enkhuizen, Netherlands, since 2003. The distinctive characteristics of this new *Saxifraga* are stable and reproduced true to type in successive generations of asexual reproduction. It takes 23 to 29 weeks to produce a finished plant, depending on the temperature.

The new *Saxifraga* plant is a perennial in all climatic zones in the US.

DESCRIPTION OF THE DRAWING

The new *Saxifraga* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Saxifraga.* The data which defines these characteristics were collected from asexual reproductions carried out in Enkhuizen, Netherlands. The plant history was taken on plants of 30 weeks old. The instant plant was grown in an 11 cm container in a plastic tunnel.

Color references are primarily to the R.H.S. Colour Chart of The Royal Horticultural Society of London.

Plants of the new *Saxifraga* differ primarily from the plants of the originator 'Purperteppich' in the following characteristics:

Plants of the new variety have uniform scarlet red flowers and a compact growth habit, whereas plants of 'Purperteppich' have red, rose and white flowers, and a loose growth habit.

TABLE 1

DIFFERENCES BETWEEN THE NEW CULTIVAR 'ROCKLET' AND A SIMILAR CULTIVAR

| | 'Rocklet' | 'Peter Pan Red' (Not patented) |
|---|---|---|
| Flower color | 71A | 63B |
| Leaf thickness | 0.4-0.5 mm | 0.7-0.8 mm |
| Time of flowering | 23-29 weeks after cutting | 26-32 weeks after cutting |

The plant:
*Classification.*—Botanical: *Saxifraga×arendsii.*
Parentage:
*Originator selection.*—'Purperteppich' (Not patented).
Propagation:
*Type of cutting.*—Terminal cuttings.
*Time to initiate roots.*—12-14 days at 18° C.
*Time to produce a rooted cutting.*—5 weeks.
*Root description.*—Fine, fibrous and white in color.
Plant description:
*General appearance.*—Makes mats of rosettes. Each rosette develops several short branches, and one or more branched flower stems.
*Growth and branching habit.*—Freely branching habit, freely flowering, vigorous.
*Plant height.*—14 cm.
*Plant spread.*—15 cm.
Lateral branches:
*Length.*—3-5 cm.
*Diameter.*—1.2 mm.
*Texture.*—Smooth; slightly pubescent with long hairs; 2-4 mm.
*Internode length.*—2-5 mm.
*Color.*—145C.

The foliage:
*Arrangement.*—Alternate.
*Shape of blade.*—Three-lobed.
*Length, mature leaves.*—0.8-1.1 cm.
*Width, mature leaves.*—0.7-1.0 cm.
*Apex.*—Acute.
*Base.*—Acute.
*Margin.*—Entire.
*Texture.*—Smooth, slightly pubescent.
*Venation pattern.*—Palmate.
*Color of upper surface.*—144A.
*Color of lower surface.*—144B.
*Venation, upper surface.*—145B.
*Venation, lower surface.*—144A.

The petiole:
*Length.*—0.7-1.0 cm.
*Width.*—1 mm.
*Color upper surface.*—144B.
*Color lower surface.*—144C.
*Texture.*—Smooth; slightly pubescent.

The flower:
*Inflorescence type.*—Each rosette develops 1-3 branched flower stems.
*Flower type.*—Single, solitary; symmetry: radial symmetric.
*Number of branches per flower stem.*—2-5.
*Number of flowers and flower buds per flower stem.*—2-15.
*Length flower stem.*—6-13 cm.
*Flower position.*—At top of branch.
*Fragrance.*—Absent.
*Flowering season.*—Spring.
*Flower diameter.*—1.2-2.4 cm.
*Lastingness of the bloom.*—40-50 days.
*Lastingness of an individual flower.*—3-6 days.

Flower buds:
*Bud length* (*at stage of showing color*).—3 mm.
*Bud diameter.*—3 mm.
*Bud shape.*—Orbicular.
*Texture.*—Smooth; pubescent, hairs have a purple tip (N79B).
*Color, just before opening.*—146B, with 63A on apex.

Petals:
*Quantity.*—5 per flower, imbricate. Some flowers develop no or smaller petals.
*Shape.*—Orbicular.
*Apex.*—Rounded to acuminate.
*Base.*—Shortly attenuate.
*Length.*—7-10 mm.
*Width.*—6-9 mm.
*Margin.*—Entire.
*Texture.*—Smooth.
*Color — upper surface.*—Young flower: 71A. Old flower: 75B.
*Color — lower surface.*—Young flower: 71B. Old flower: 75B.
*Venation pattern.*—Bowed.
*Venation upper surface.*—59B.
*Venation lower surface.*—199D.

Sepals:
*Quantity.*—5 per flower.
*Shape.*—Ovate.
*Apex.*—Acute.
*Margin.*—Entire.
*Length.*—3-4 mm.
*Width.*—2.5-3.5 mm.
*Color — upper surface.*—146B, with some 63A on apex.
*Color — lower surface.*—146C.
*Texture upper surface.*—Smooth; slightly pubescent, hairs have a purple tip (N79B).
*Texture lower surface.*—Smooth, glabrous.

Peduncles:
*Length.*—0.5-3.0 cm.
*Diameter.*—1 mm.
*Color.*—144A with much anthocyanin 60A.
*Texture.*—Smooth; pubescent, hairs have a purple tip (N79B).

Reproductive organs:
*Androecium.*—Stamen number: 10, not fused. Filament length: 3-5 mm. Filament shape: Threadlike. Filament color: 154B. Anther shape: Bi-lobed. Anther length: 1.5 mm. Anther color: 149A with anhocyanin 63A. Color of pollen: 2A. Amount of pollen: Normal.
*Gynoecium.*—Pistil number: 2. Pistil length: 3-4 mm. Stigma color: 155A. Style color: 1B. Ovary color: 150A.

Seed development: Seed development has not been observed to date.

Disease/pest resistance: No disease/pest resistance has been observed to date.

What is claimed is:

1. A new and distinct cultivar of *Saxifraga* plant named 'Rocklet,' as substantially illustrated and described herein.

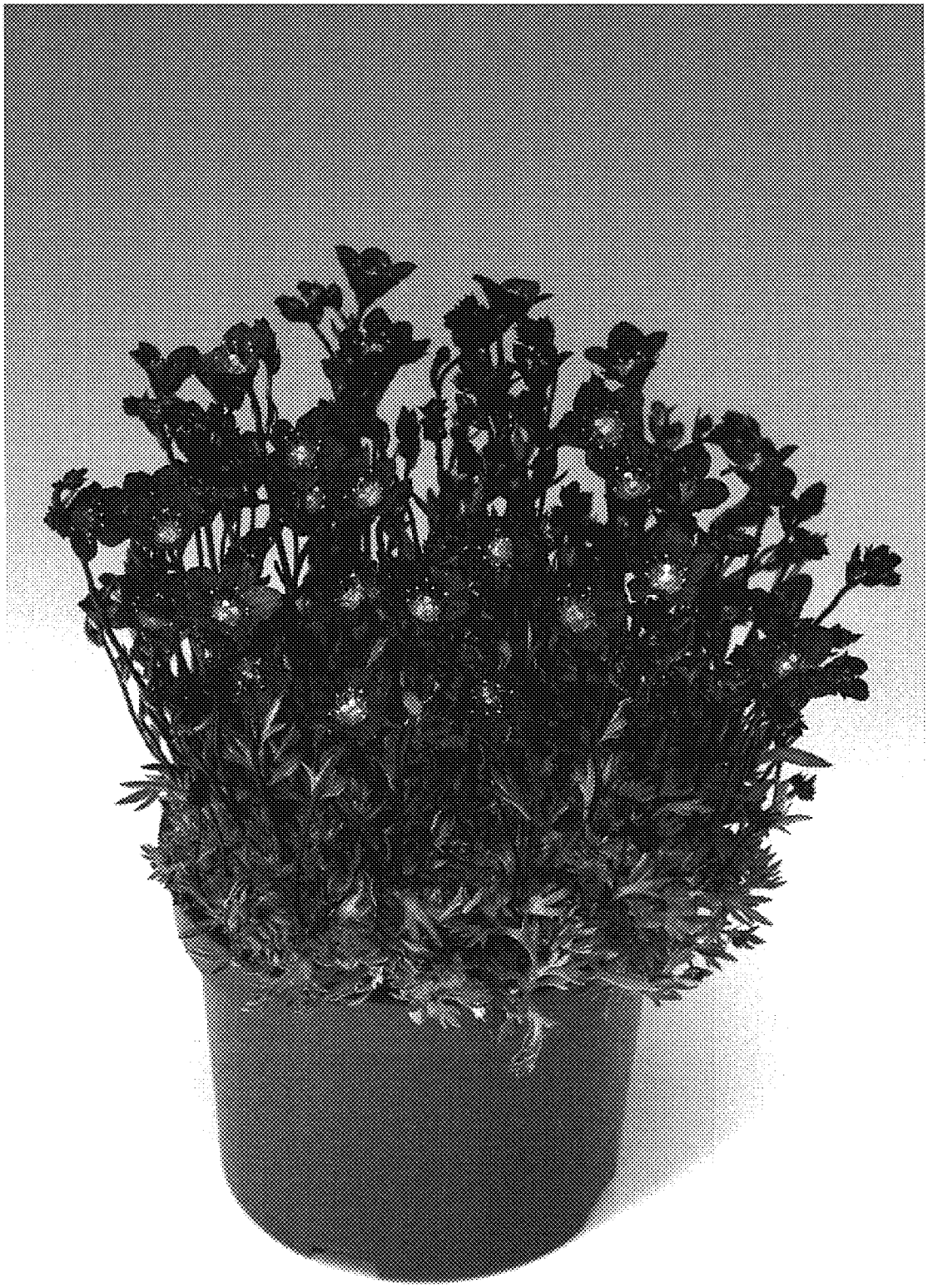

* * * * *